(12) United States Patent
Levitsky et al.

(10) Patent No.: US 10,820,834 B2
(45) Date of Patent: Nov. 3, 2020

(54) FLUID DRYING MECHANISM

(71) Applicant: ORIDION MEDICAL 1987 LTD., Jerusalem (IL)

(72) Inventors: Gershon Levitsky, Jerusalem (IL); Joshua Lewis Colman, Jerusalem (IL)

(73) Assignee: ORIDION MEDICAL 1987 LTD., Jerusalem (IL)

( * ) Notice: Subject to any disclaimer, the term of this patent is extended or adjusted under 35 U.S.C. 154(b) by 692 days.

(21) Appl. No.: 15/610,261

(22) Filed: May 31, 2017

(65) Prior Publication Data

US 2017/0265779 A1    Sep. 21, 2017

Related U.S. Application Data

(63) Continuation of application No. 14/677,967, filed on Apr. 2, 2015, now abandoned, which is a continuation
(Continued)

(51) Int. Cl.
| | |
|---|---|
| *A61B 5/097* | (2006.01) |
| *A61M 16/10* | (2006.01) |
| *A61M 16/08* | (2006.01) |

(52) U.S. Cl.
CPC .............. *A61B 5/097* (2013.01); *A61M 16/08* (2013.01); *A61M 16/085* (2014.02);
(Continued)

(58) Field of Classification Search
CPC .. A61M 16/16; A61M 16/00; A61M 16/0666; A61M 16/1045; A61M 16/085;
(Continued)

(56) References Cited

U.S. PATENT DOCUMENTS

| | | | |
|---|---|---|---|
| 3,452,366 A | 7/1969 | Downey et al. | |
| 3,735,558 A | 5/1973 | Skarstrom et al. | |

(Continued)

FOREIGN PATENT DOCUMENTS

| | | | |
|---|---|---|---|
| EP | 190388 A2 | 8/1986 | |
| WO | 2006070366 A2 | 7/2006 | |

(Continued)

OTHER PUBLICATIONS

EN 1707:1996 Conical fittings with 6% (Luer) taper—for syringes, needles and certain other medical equipment—Lock Fittings.
(Continued)

*Primary Examiner* — Kathryn E Ditmer
(74) *Attorney, Agent, or Firm* — Cantor Colburn LLP

(57) ABSTRACT

There is provided an exhaled breath moisture reduction system including a dryer mechanism and a connector adapted to connect the dryer mechanism proximate to a respiratory output device. There is also provided an exhaled breath sampling assembly including an airway adaptor and a moisture reduction sleeve comprising a material adapted to reduce moisture and a connector adapted to connect said sleeve substantially adjacent to a breath sampling inlet within the adaptor. Also provided, a method of sampling breath which includes attaching an exhaled breath moisture reduction sleeve substantially adjacent to a breath sampling inlet.

17 Claims, 6 Drawing Sheets

Related U.S. Application Data of application No. 14/191,394, filed on Feb. 26, 2014, now abandoned, which is a continuation of application No. 11/914,135, filed as application No. PCT/IL2006/000554 on May 10, 2006, now Pat. No. 9,757,052.

(60) Provisional application No. 60/679,890, filed on May 10, 2005.

(52) U.S. Cl.
CPC .... *A61M 16/0816* (2013.01); *A61M 16/1065* (2014.02); *A61M 16/0808* (2013.01); *A61M 2205/3633* (2013.01); *A61M 2230/432* (2013.01)

(58) Field of Classification Search
CPC ............... A61M 16/10; A61M 16/105; A61M 16/0003; A61M 16/0093; A61M 2016/103; A61M 2205/7536; A61M 2016/0413; A61M 2202/062; A61M 2205/7527; A61M 2205/125; A61M 2039/1083; A61M 2039/1088; A61B 5/097; A61B 5/08; A61B 5/0836; A61B 5/083; A61B 5/082; G01N 33/497; G01N 1/2205; G01N 33/4972; G01N 1/2202; G01N 1/22; G01N 1/2247; G01N 1/2035; G01N 2001/2244; G01N 33/0011; G01N 1/02; G01N 2033/4975; G01N 2030/146; G01N 31/223; G01N 2030/025; G01N 2021/0193; B01D 53/26; B01D 53/263; B01D 53/268

See application file for complete search history.

(56) References Cited

U.S. PATENT DOCUMENTS

| | | | |
|---|---|---|---|
| 4,285,699 A | | 8/1981 | Itoh |
| 4,446,869 A | * | 5/1984 | Knodle .................. A61B 5/097 128/205.12 |
| 4,456,014 A | | 6/1984 | Buck et al. |
| 4,509,359 A | * | 4/1985 | Gedeon .................. A61B 5/083 600/532 |
| 4,558,708 A | | 12/1985 | Labuda et al. |
| 4,677,987 A | * | 7/1987 | Choksi .................. A61B 5/097 422/84 |
| 4,705,543 A | * | 11/1987 | Kertzman ............ B01D 53/268 210/490 |
| 4,808,201 A | * | 2/1989 | Kertzman ............ B01D 53/268 210/490 |
| 4,815,459 A | * | 3/1989 | Beran .................... A61B 5/097 128/207.14 |
| 5,042,500 A | * | 8/1991 | Norlien .................. A61B 5/083 128/205.12 |
| 5,047,021 A | | 9/1991 | Utterberg et al. |
| 5,129,401 A | | 7/1992 | Corenman et al. |
| 5,131,387 A | | 7/1992 | French et al. |
| 5,143,695 A | * | 9/1992 | van den Burg .......... G01N 1/24 422/84 |
| 5,233,996 A | | 8/1993 | Coleman et al. |
| 5,377,670 A | | 1/1995 | Smith et al. |
| 5,501,212 A | * | 3/1996 | Psaros ................. A61M 16/009 128/204.16 |
| 5,616,158 A | | 4/1997 | Biendarra et al. |
| 5,657,750 A | | 8/1997 | Colman et al. |
| 5,824,919 A | | 10/1998 | Hansen |
| 5,857,461 A | * | 1/1999 | Levitsky ................ A61B 5/083 128/204.16 |
| 5,996,976 A | | 12/1999 | Murphy et al. |
| 6,063,062 A | | 5/2000 | Paradis et al. |
| 6,089,541 A | | 7/2000 | Weinheimer et al. |
| 6,437,316 B1 | | 8/2002 | Colman |
| 6,474,335 B1 | | 11/2002 | Lammers |
| 6,508,807 B1 | | 1/2003 | Peters |
| 6,722,705 B2 | | 4/2004 | Korkor |
| 6,779,522 B2 | * | 8/2004 | Smith .................... A61M 16/08 128/203.16 |
| 6,783,573 B2 | * | 8/2004 | Richardson ......... A61M 16/085 96/6 |
| 7,051,604 B1 | | 5/2006 | Mayeaux |
| 7,086,399 B2 | | 8/2006 | Makinson et al. |
| 8,123,727 B2 | | 2/2012 | Luther et al. |
| 2001/0031224 A1 | | 10/2001 | Labuda et al. |
| 2002/0017300 A1 | | 2/2002 | Hickle et al. |
| 2003/0191405 A1 | * | 10/2003 | Rich ...................... A61B 5/097 600/532 |
| 2004/0060443 A1 | | 4/2004 | Richardson |
| 2004/0210153 A1 | | 10/2004 | Tsukashima et al. |
| 2004/0226566 A1 | * | 11/2004 | Gunaratnam ..... A61M 16/0683 128/207.18 |
| 2005/0087715 A1 | | 4/2005 | Doyle |
| 2005/0161042 A1 | | 7/2005 | Fudge et al. |
| 2006/0021615 A1 | | 2/2006 | Kertzman |
| 2006/0086254 A1 | | 4/2006 | Fudge et al. |
| 2008/0265191 A1 | | 10/2008 | Walborn |
| 2009/0281443 A1 | | 11/2009 | Hengstenberg et al. |

FOREIGN PATENT DOCUMENTS

| | | |
|---|---|---|
| WO | 2006120683 A2 | 11/2006 |
| WO | 2008144513 A1 | 11/2008 |

OTHER PUBLICATIONS

European Search Report; Application No. 12858318.4, Completed Aug. 24, 2015, dated Sep. 2, 2015, 6 pages.
Foulger and Simmonds (1979) Drier for field use in the determination of trace atmospheric gases. Anal Chem 51(7): 1089-1090.
International Search Report; PCT Application No. PCT/IL06/00554; dated Apr. 10, 2007.
Examination Report for European Application No. 06745092.4 dated Oct. 22, 2018; 7 pgs.
EP Application No. 06745092.4 Extended EP Search Report dated Apr. 7, 2017, 8 pages.

* cited by examiner

FLUID DRYING MECHANISM

CROSS-REFERENCE TO RELATED APPLICATIONS

This application is a Continuation of U.S. application Ser. No. 14/677,967, filed Jul. 27, 2014 (published as 2015/0208953), which is a Continuation of U.S. application Ser. No. 14/191,394, filed Feb. 26, 2014 (published as US 2014/0180157), which is a Continuation of U.S. application Ser. No. 11/914,135, filed Nov. 11, 2007 (published as US 2009/0088656), which is the U.S. National Stage of International Application No. PCT/IL2006/000554, filed May 10, 2006, which claims the benefit of U.S. Provisional Application No. 60/679,890, filed May 10, 2005, the contents of each of which are hereby incorporated by reference in their entireties.

FIELD OF THE DISCLOSURE

The present disclosure generally relates to fluid drying tube(s), particularity for use in the field of breath sampling and analysis.

BACKGROUND

Breath gas analysis is commonly performed to provide information related to a patient's condition. An example of a gas analysis often performed is capnography using an analyzer called a capnograph. Capnography is the monitoring of the time dependent respiratory carbon dioxide ($CO_2$) concentration, which may be used to directly monitor the inhaled and exhaled concentration of $CO_2$, and indirectly monitor the $CO_2$ concentration in a patient's blood. Capnography may provide information about $CO_2$ production, pulmonary (lung) perfusion, alveolar ventilation (alveoli are hollow cavities in the lungs in which gas exchange is being performed) and respiratory patterns. Capnography may also provide information related to a patient's condition during anaesthesia, for example by monitoring the elimination of $CO_2$ from anaesthesia breathing circuit and ventilator.

In breath analysis systems, for example capnography, breath gas can be sampled either by a mainstream or a sidestream analyzer. In mainstream analyzers the sample chamber is positioned within the patient's gas stream near the patient's end of the breathing system. This arrangement is normally heavier and more cumbersome.

In sidestream analysers gas is drawn from the breathing system by a tube. The tube, which may be connected to an adaptor near the patient's end of the breathing system, delivers the gas to a sampling place (such as a sampling chamber). There are several elements that are generally common to sidestream breath analysis systems (such as capnographs) including, a monitor that continuously samples and monitors the $CO_2$ in a patients breath, airway tube(s) and sampling line(s) which may be flexible tube(s) having narrower diameter(s) than the airway tube(s), and are adapted used to connect between the patient airway tube(s) and the distant analyzer, such as the capnograph monitor. Along this tube, the patient's breath is continuously sampled.

It is usually preferable that the sampling line is clear of liquids in the fluid sample at all times, in order to permit continuous, non-interfered monitoring. Such liquids are common in patient sampling systems, and have several origins, for example:

- condensed out liquids from the highly humidified air provided to and exhaled from the patient. These liquids typically accumulate both in the patient airway and in the sampling line tubing;
- secretions from the patient, typically found in the patient airway; and
- medications or saline solution provided to the patient during Lavage, suction and nebulization procedures.

Condensed out liquids generally refer to water that condenses out from the humidity (the water vapor in a air or in other gas) in the sampling tubes. Condensed out liquids is a major problem commonly hindering breath analyses, particularly sidestream capnography. The internal humidity levels in the tubes are high especially in proximity to the breath collection area since the exhaled and inhaled breath is humid and relatively warm. This is also the case in intubated patients who are generally artificially ventilated with gas (for example, air) having up to 100% humidity at a temperature normally above ambient temperature (for example, about 34° C.), depending on the airway humidification system and patient needs. The humidity (water vapors) often condenses on the tube particularly as the tube is extended farther from the breath collection area due to the temperature decreases.

Several methods have been developed in order to keep the sampling line free of liquids such as those mentioned above, particularly moisture. Some methods are designed to prevent liquids from entering the sampling line (for example, as described in U.S. Pat. No. 5,857,461) and some are designed to remove such liquids if they entered the sampling line or were created in it.

In addition to the aforementioned preventive steps, it is common practice in side-stream capnography to use tubes that are made of or include drying materials. The internal humidity levels in the tubes, especially in proximity to the breath collection area, are high, and since airway temperature, dictated by the airway humidification system and patient needs, is relatively high, there is a clear need for a material which will bring down the internal humidity of the sampled breath before the humid gas would condense out when flowing towards the gas analyzer (for example capnograph), cooled by the ambient air. One such suitable material is Nafion®.

Nafion® is a copolymer of tetrafluoroethylene (Teflon®) and perfluoro-3,6-dioxa-4-methyl-7-octene-sulfonic acid. Like Teflon, Nafion® is highly resistant to chemical attack, but the presence of its exposed sulfonic acid groups confers unusual properties. Sulfonic acid has a very high water-of-hydration, absorbing 13 molecules of water for every sulfonic acid group in the polymer; consequently, Nafion® absorbs 22% by weight of water. Since the Nafion® specifically reacts with water, gases being dried or processed are usually entirely unaffected. Nafion® tubing, which comprises an ion exchanger, has the ability to equate internal humidity levels with the external ambient humidity.

The efficiency of drying materials such as Nafion® in dehumidifying a gas sample is dependant mainly on the following parameters:

- the rate of flow of gas passing through the drying tube (a tube that include a drying material such as Nafion®), wherein the slower the flow rate, the more efficient is the dehumidifying process;
- the tube diameter, wherein the smaller the diameter, the more efficient is the dehumidifying process;
- the wall thickness, wherein the thinner the wall, the more efficient is the dehumidifying process;

the humidity gradient inside and outside of the tube, wherein the greater the difference in humidity inside and outside, the more efficient is the dehumidifying process;

the temperature of the humid gas, wherein the higher the temperature, the more efficient is the dehumidifying process; and The movement of air around the drying tube (such as Nafion® tube); wherein the faster the movement, the more efficient is the dehumidifying process.

Materials like Nafion® tend to be expensive and their cost is dependant on the length of material required. Since gas sampling lines (for example in a capnograph) are disposable in nature, one must design the sample line including the Nafion® tube in the most effective way so as to use the least amount of drying material such as Nafion® necessary for the purpose required. Hence one must use the above listed parameters in order to provide the optimal solution.

Further, the patient airway tubes are typically furnished with large diameters, to address large flows of gas, typically up to about 30 liters per minute. Such patient airway tubes may use heating systems to keep the humidified air from condensing out. On the other hand, gas sampling lines (for example in a capnograph) often use small (internal and external) diameter bore tubings to enable the undisturbed flow of the sampled breath at low flow rates, such as about 50 ml/min. The substantial change in diameters between the patient airway tubes and the sampling tubes may create rapid drop in temperatures when passing from the patient airway, through the sampling port to the sample line. This temperature drop results in rapid condensation of the humidified breath before reaching the drying tube (which may include for example, Nafion®), and hence before the internal humidity can be equated with the lower ambient humidity. Since the temperature generally drops significantly before the gas reaches the drying material (while as aforementioned, drying materials such as Nafion® operate more efficiently at higher temperatures) and since water may have already condensed out in the sampling line before the gas reaches the drying material (while drying materials such as Nafion® are more efficient in removing humidity than water), drying material such as Nafion® are often used in an ineffective manner. Prior art refers to the problem of moisture in gas sampling tubes. U.S. Pat. No. 6,783,573, for example, refers to the "moisture problem" and teaches away from placing a dryer mechanism in the connector adjacent to, or proximate to, the respiratory output device (e.g., the mask, cannula, or etc.). U.S. Pat. No. 6,783,573 specifically states that this approach has drawbacks. Moreover, U.S. Pat. No. 6,783,573 states "the dryer mechanism disposed proximate the patient is ineffective, . . . " (column 1, lines 64-65). U.S. Pat. No. 6,783,573.

There is thus a need for sampling systems that are adapted to reduce the amount of liquids, particularly moisture, that form along the sampling tubes.

SUMMARY

The following embodiments and aspects thereof are described and illustrated in conjunction with systems, tools and methods, which are meant to be exemplary and illustrative, not limiting in scope. In various embodiments, one or more of the above-described problems have been reduced or eliminated, while other embodiments are directed to other advantages or improvements.

In accordance with some embodiments, there is provided an exhaled breath moisture reduction system including a dryer mechanism and a connector adapted to connect the dryer mechanism proximate to a respiratory output device.

The connector may be adapted to connect between a dryer mechanism and a respiratory output device in such way that substantially retains the gas sample characteristics (for example, humidity and temperature) until it reaches the dryer mechanism.

In accordance with some embodiments, there is provided an exhaled breath moisture reduction system including a dryer mechanism adjacent to a connector adapted to connect the dryer mechanism to a respiratory output device, wherein the dryer mechanism comprises a reinforcing element.

In accordance with additional embodiments, there is provided an exhaled breath moisture reduction sleeve including a material adapted to reduce moisture and a connector adapted to connect the sleeve substantially adjacent to a breath sampling inlet.

In accordance with additional embodiments, there is provided an exhaled breath sampling assembly including an airway adaptor and a moisture reduction sleeve comprising a material adapted to reduce moisture and a connector adapted to connect the sleeve substantially adjacent to a breath sampling inlet within the adaptor.

In accordance with some embodiments of the present disclosure, there is provided an exhaled breath sampling assembly including a cannula, a moisture reduction sleeve including a material adapted to reduce moisture, and a connector adapted to connect the sleeve substantially adjacent to a breath sampling inlet within the cannula, wherein the sleeve is adapted to be placed on a subject's face.

In accordance with additional embodiments, there is provided a breath analyzer including a moisture reduction sleeve comprising a material adapted to reduce moisture and a connector adapted to connect the sleeve substantially adjacent to a breath sampling inlet.

In accordance with additional embodiments, there is provided a method of sampling breath including attaching an exhaled breath moisture reduction sleeve substantially adjacent to a breath sampling inlet.

In accordance with other embodiments, there is provided a method of sampling breath including attaching an exhaled breath moisture reduction sleeve substantially adjacent to a breath sampling inlet of a cannula, wherein the moisture reduction sleeve is placed on a subject's face.

In addition to the exemplary aspects and embodiments described above, further aspects and embodiments will become apparent by reference to the figures and by study of the following detailed description.

BRIEF DESCRIPTION OF THE FIGURES

Exemplary embodiments are illustrated in referenced figures. It is intended that the embodiments and figures disclosed herein are to be considered illustrative, rather than restrictive. The disclosure, however, both as to organization and method of operation, together with objects, features, and advantages thereof, may best be understood by reference to the following detailed description when read with the accompanying figures, in which.

Figure 1:
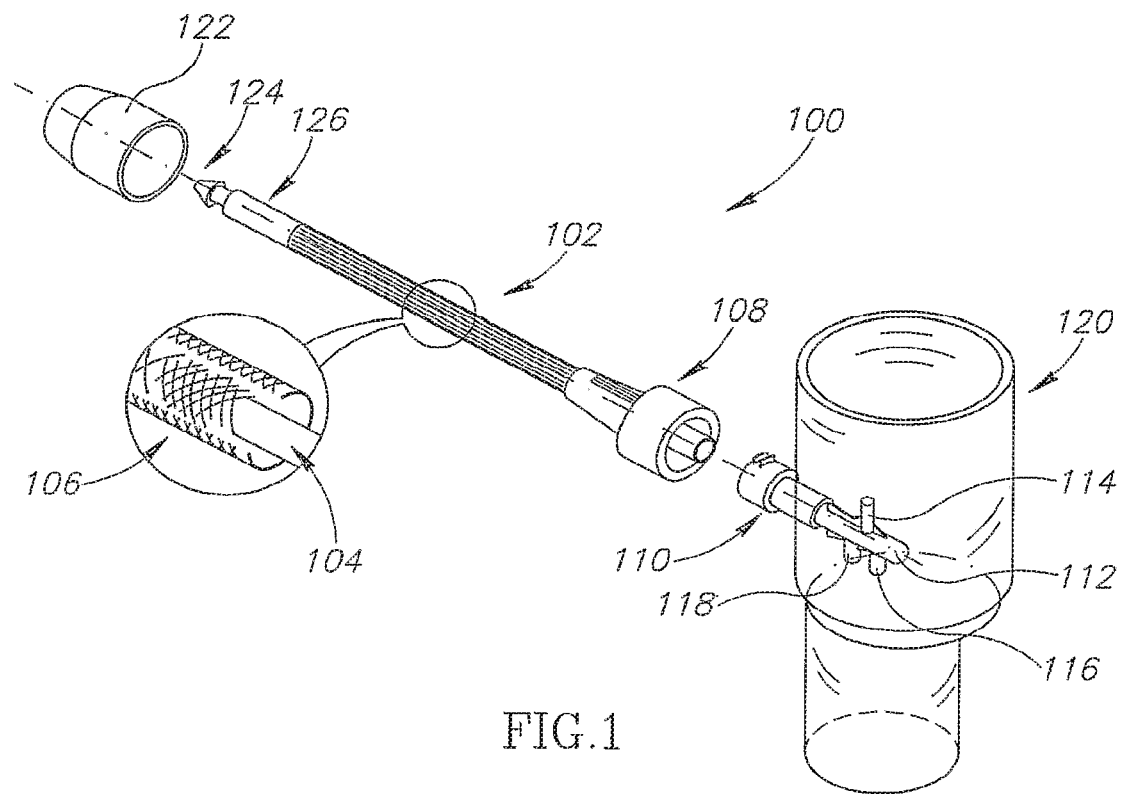
FIG. 1 schematically illustrates an exploded view of a sampling system constructed and operative in accordance with some embodiment of the present disclosure.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION

While a number of exemplary aspects and embodiments have been discussed above, those of skill in the art will recognize certain modifications, permutations, additions and sub-combinations thereof. It is therefore intended that the following appended claims and claims hereafter introduced be interpreted to include all such modifications, permutations, additions and sub-combinations as are within their true spirit and scope.

As discussed hereinabove there is a need for sampling systems that are adapted to reduce the amount of liquids, particularly moisture, that are formed along and/or within the sampling tubes. It was found that implanting a dryer mechanism (such as but not limited to a dryer tube that may include, for example, Nafion®) within (in such way that the drying material is not in direct contact with the highly humid ambient environment) or otherwise associated with the airway adaptor or as close to the airway adaptor as possible reduces the amount of liquids, particularly moisture in the sampling system.

The airway adaptor, which may be a part of a respiratory output device or may be adapted to fit into a respiratory output device, is adapted to allow the transfer of the warmed air of the patient's airway flow (from either natural breathing or artificial ventilation) and is generally disposed near the patient. Particularly, the airway adaptor may be a part of or fit into a respiratory output device, which is adapted for use in intubated patients, for example patients being artificially ventilated. A respiratory output device may be for example, a mask, airway tube, endotracheal tube, intubation tube and the like.

The dryer mechanism may preferably be disposed adjacent to, or proximate to, the airway adaptor and/or the respiratory output device (for example, a mask, cannula, an airway tube, endotracheal tube, intubation tube and the like) in such a way that the warmed air in the patient's airway flow (from either natural breathing or artificial ventilation) heats the dryer mechanism (such as but not limited to, a dryer tube that may include for example, Nafion®), thus maintaining a higher temperature of the humid gas, increasing the efficiency of the dryer mechanism and reducing humidity in the sampled gas. Additionally, an isolator, for example, formed of a foamy material, may be placed around the region connecting between the dryer mechanism and the breath sampling inlet, in order to maintain the temperature of the humid gas when reaching the dryer mechanism.

It is noted that in the drying material of the dryer mechanism (for example, Nafion® tube) may be preferably placed adjacent to, or proximate to, the airway adaptor and/or the respiratory output device in such way were it is not in the direct stream of the patients exhaled breath, since this would create a high ambient humidity environment to the drying material, and as mentioned hereinabove, the dryer material is more efficient when the gradient between inside and outside is large.

Provided herein, according to embodiments of the disclosure, configurations in which the warmed air of the patient's airway flow (from either natural breathing or artificial ventilation) heats the dryer mechanism and thus maintain a higher temperature of the humid gas. These configurations increase the efficiency of the dryer mechanism and reduce humidity and/or moisture in the sampled gas as well as to prevent any liquids condensing out prior to reaching the dryer mechanism, for example, dryer tube, (as mentioned herein, condensed out liquids reaching the, render the dryer mechanism, for example, dryer tube, less efficient by a cooling effect, in other words, the dryer mechanism should preferably be used to dehumidify rather than to remove water). The dryer mechanism, for example, may be wound around the airway adaptor to increase its temperature (and the temperature of the gas flowing through it) and thus the dryer mechanism's efficiency.

In accordance with some embodiments of the present disclosure, particularly when used with a cannula, for example with non-intubated patients that are anyway wearing a cannula that is secured upon the patients face, the dryer mechanism, for example, Nafion® tube, may be placed on or near the patient's face, as close as possible to the cannula so as to gain heat from the patient. There is thus provided, in accordance with some embodiments of the present disclosure, an exhaled breath sampling assembly including a cannula, a moisture reduction sleeve including a material adapted to reduce moisture, and a connector adapted to connect the sleeve substantially adjacent to a breath sampling inlet within the cannula, wherein the sleeve is adapted to be placed on a subject's face.

In accordance with some embodiments, there is provided an exhaled breath moisture reduction system including a dryer mechanism and a connector adapted to connect the dryer mechanism proximate to a respiratory output device. The connector may be adapted to connect between a dryer mechanism and a respiratory output device in such way that substantially retains the gas sample characteristics (for example, humidity and temperature) until it reaches the dryer mechanism. The connector may be molded on the dryer mechanism and/or a separate element. The dryer mechanism may include a material adapted to absorb moisture. The dryer mechanism may include a material adapted to pass moisture.

When used, the respiratory output device is generally maintained at a temperature higher than ambient temperature, because it passes the exhaled breath of a subject. The proximity between the dryer mechanism and the respiratory output device may allow maintaining the dryer mechanism at a relatively high temperature and thus increase the efficiency of the moisture (and/or humidity) reduction. The system may further include a gripper adapted to cover or partially cover the connector. In addition to being a grabbing point, the gripper may include an insulating material. The insulating material may be a thermal insulator and may be adapted to maintain the relatively high temperature of the gas passing from the respiratory output device to the dryer mechanism.

The term "proximate to" may refer to 3 cm (centimeters) or less, for example, 1 cm or less, 0.5 cm or less). The closer the dryer mechanism to the respiratory output device, the less heat is lost.

In accordance with some embodiments, there is provided an exhaled breath moisture reduction system including a dryer mechanism adjacent to a connector adapted to connect the dryer mechanism to a respiratory output device, wherein the dryer mechanism comprises a reinforcing element.

The connector may be adapted to connect between a dryer mechanism and a respiratory output device in such way that substantially retains the gas sample characteristics (for example, humidity and temperature) until it reaches the dryer mechanism.

The dryer mechanism may include a material adapted to absorb moisture. The dryer mechanism may include a material adapted to pass moisture.

The proximity between the dryer mechanism and the connector to the respiratory output device may allow maintaining the dryer mechanism at a relatively high temperature and thus increase the efficiency of the moisture (and/or humidity) reduction.

The term "adjacent to" may refer to 3 cm (centimeters) or less, for example, 1 cm or less, 0.5 cm or less). "Adjacent to" may also include a connector that is molded on the dryer mechanism.

In accordance with additional embodiments, there is provided an exhaled breath moisture reduction sleeve including material(s) adapted to reduce moisture and a connector adapted to connect the sleeve substantially adjacent to a breath sampling inlet.

In accordance with additional embodiments, there is provided an exhaled breath sampling assembly including an airway adaptor and a moisture reduction sleeve comprising a material adapted to reduce moisture and a connector adapted to connect the sleeve substantially adjacent to a breath sampling inlet within the adaptor.

In accordance with additional embodiments, there is provided a breath analyzer including a moisture reduction sleeve comprising a material adapted to reduce moisture and a connector adapted to connect the sleeve substantially adjacent to a breath sampling inlet.

The connector may be adapted to connect between a dryer mechanism and a respiratory output device in such way that substantially retains the gas sample characteristics (for example, humidity and temperature) until it reaches the dryer mechanism.

The dryer mechanism may include a material adapted to absorb moisture. The dryer mechanism may include a material adapted to pass moisture.

In accordance with additional embodiments, there is provided a method of sampling breath including attaching an exhaled breath moisture reduction sleeve substantially adjacent to a breath sampling inlet (which may be within an airway adaptor). Attaching an exhaled breath moisture reduction sleeve substantially adjacent to a breath sampling inlet may be performed in such way as to substantially retains the gas sample characteristics (for example, high temperature) until it reaches the dryer mechanism and thus increase the efficiency of the dryer mechanism.

In accordance with other embodiments, there is provided a method of sampling breath including attaching an exhaled breath moisture reduction sleeve substantially adjacent to a breath sampling inlet of a cannula, wherein the moisture reduction sleeve is placed on a subject's face. Attaching an exhaled breath moisture reduction sleeve substantially adjacent to a breath sampling inlet of a cannula and placing the moisture reduction sleeve on a subject's face may allow substantial retaining of the gas sample characteristics (for example, high temperature) until it reaches the dryer mechanism and thus increase the efficiency of the dryer mechanism.

A "connector" as referred to herein may include any element that is adapted to bring to objects close to each other. A connector may refer to a molded-on connector, which may be a part of the drying mechanism and/or a separate element.

A "dryer mechanism" (or a drying mechanism) as referred to herein may include a dryer tube, a dryer sleeve that include material(s) capable of absorbing or passing moisture and/or humidity from a fluid such as exhaled breath. The dryer mechanism may have any other form, for example a sheet that allows reduction of humidity in sampled exhaled breath while maintaining the spacial resolution (and/or special integrity) of the collected breath samples. The dryer mechanism may include for example, Nafion®. The dryer mechanism (such as the dryer tube) may include a reinforcing element.

A "reinforcing element" as referred to herein may include any element adapted to provide mechanical protection to the dryer mechanism, for example, prevent fluid flow interruption, damaging, (partially) blocking, bending and/or collapsing of the drying tube. The reinforcing element may cover essentially or a portion of a dryer mechanism. The reinforcing element may include, for example, a braiding net or any other form of mechanical support, such as rigids, rods or the like.

A "respiratory output device" as referred to herein may include, a mask, cannula, airway tube, endotracheal tube, intubation tube and the like.

A "breath sampling inlet" as referred to herein may include an opening, aperture, orifice, valve or the like that is adapted for collection of fluid (such as breath exhale) from a subject's airway (such as an airway adaptor, cannula, airway tube or the like).

A "sleeve" as referred to herein may include a replaceable cylinder or a jacket that may include or be embodied by a drying material. A "sleeve" may also refer to a cylindrically shaped or otherwise tubular piece that sits over or under a rod, joint, shaft or tube.

A "cannula" as referred to herein may include different types of oral/nasal cannula(s), which may be used to deliver oxygen to patients who require assistance to breath properly and/or to collect breath samples from patients to monitor respiration, or to perform both functions. Such cannula(s) may be used when direct ventilation is not provided. The term "oral/nasal" may refer to the adaptable configuration of such cannula(s) which are designed to be in close proximity to the oral cavity and/or nasal cavity and may also be at least partially inserted into the nasal cavity.

Figure 2:
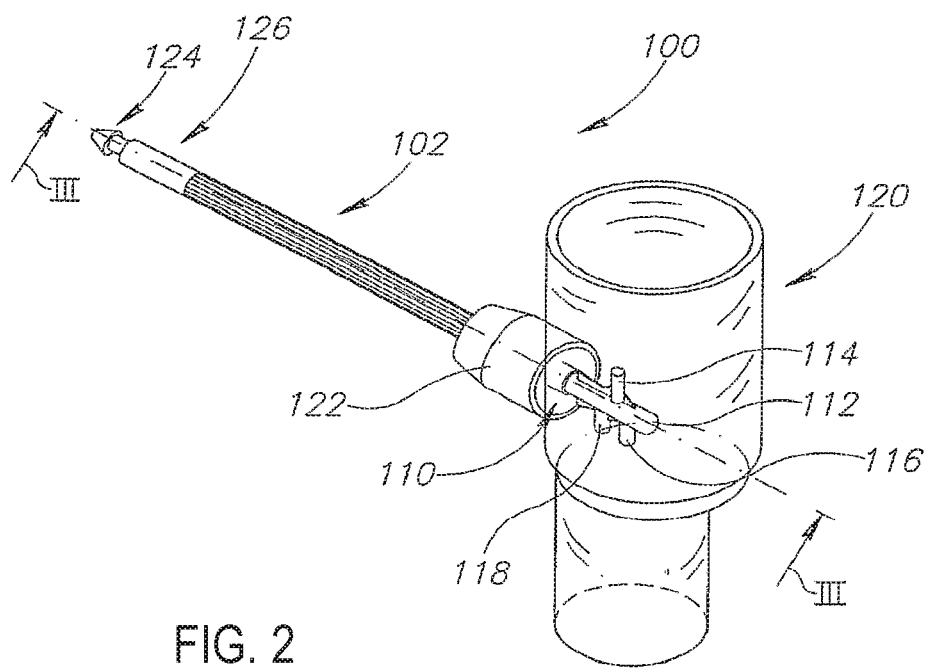
FIG. 2 schematically illustrates an assembled view of the sampling system of FIG. 1.

Reference is now made to FIG. 1, which schematically illustrates an exploded view of a sampling system constructed and operative in accordance with some embodiment of the present disclosure and to FIG. 2, which schematically illustrates an assembled view of the sampling system of FIG. 1. The sampling system 100 is adapted for sampling and analysis of exhaled breath, while reducing the exhaled breath moisture using a moisture reduction system 102 adapted to position a dryer mechanism proximate to a respiratory output device (such as a mask, cannula, oral and/or nasal breath collectors, endotracheal tube intubation tube and the like). The respiratory output device is generally located near the patient.

The sampling system 100 includes a moisture reduction system 102, which includes a dryer mechanism, particularly a dryer tube 104 and a reinforcing element 106. The moisture reduction system 102 further includes a connector 108 that is adapted to connect the dryer tube 104 substantially adjacent to a breath sampling inlet 110. The breath sampling inlet 110 is adapted to connect between the connector 108 and the airway adaptor 120 which may be a part of the respiratory output device (particularly, endotracheal tube, intubation tube and the like). The breath sampling inlet 110 may be integrally formed with the airway adaptor 120 (as shown) or may be attached to the airway adaptor 120. The airway adaptor 120 is adapted to connect to a patient respiratory gas output mechanism such as an endotracheal tube or intubating tube. The breath sampling inlet 110 is shown (partially) within an airway adaptor 120. The breath sampling inlet 110 further includes a sampler 112 having sampling prongs 114, 116 and 118 which are adapted to collect exhaled (and also inhaled) breath. Of course, sampler 112 may be structured differently, for example in deferent length, position within the airway adaptor 120, angle, number and position of sampling prongs and the like. The sampler 112 may include openings and/or funnel shaped collectors instead of one or more prongs and/or may include, for example one or more (for example 1, 2, 3 or more) prongs in each one of the sampling sides.

The moisture reduction system 102 further includes a gripper 122, which is adapted to (at least partially) cover the connector 108 (as shown in FIG. 2) and may allow the attendant (technician, nurse and the like) to handle the sampling system 100 without touching and possibly damaging the dryer tube 104.

The moisture reduction system 102 further includes a molded-on connector 126 having a male adaptor 124, which is adapted to connect to the sampling tubing (not shown). The molded-on connector 126 also provides a mechanical protection to the dryer tube 104 (which is often of a frail nature).

It is noted that other appropriate connectors and/or adaptors, which may have different shapes and/or operative mechanisms, may be used. The sampling tubing may further include another moisture reduction system (not shown), which may be the same or different from moisture reduction system 102 and a coupler that allows the connection of the sampling system 100 to a gas analyzer such as a capnograph (not shown).

The dryer tube 104 may include any drying mechanism and/or material that is capable of reducing the moisture level in the sampling system 100 and the sampling tubes. For example, the dryer tube 104 may include Nafion® as referred to herein. In another example, the dryer tube 104 may include filters such as microporous filters or molecular sieves (material containing tiny pores of a precise and uniform size that may be used to absorb moisture). The dryer tube 104 may vary in length and/or in diameter. It is generally preferable that the dryer tube is adapted to absorb moisture and is essentially impermeable to gases. A filter of molecular sieve into which certain materials are impregnated may be included in the drying tube. The reinforcing element 106 is adapted to provide mechanical protection to the drying tube 104, for example prevent flow interruption, damaging, (partially) blocking, bending and/or collapsing of the drying tube 104. The reinforcing element 106 may cover a portion of the drying tube 104. The reinforcing element 106 may include, for example, a braiding net (as shown in FIG. 1) or any other form of mechanical support, such as rigid bars.

The connector 108 that is adapted to connect the dryer tube 104 substantially adjacent to the breath sampling inlet 110 may vary in shape and or size, for example in a way that would allow minimizing the distance between the dryer tube 104 and the breath sampling inlet 110.

The gripper 122 may include an insulating material. The insulating material may be a thermal insulator (made for example from a foamy material) that allows maintaining relatively high temperature of the sampled breath prior to reaching the dryer tube 104. Maintaining relatively high temperature of the sampled breath will in turn reduce the condensing out of water and thus increase the efficiency of the dryer tube 104.

Figure 3:
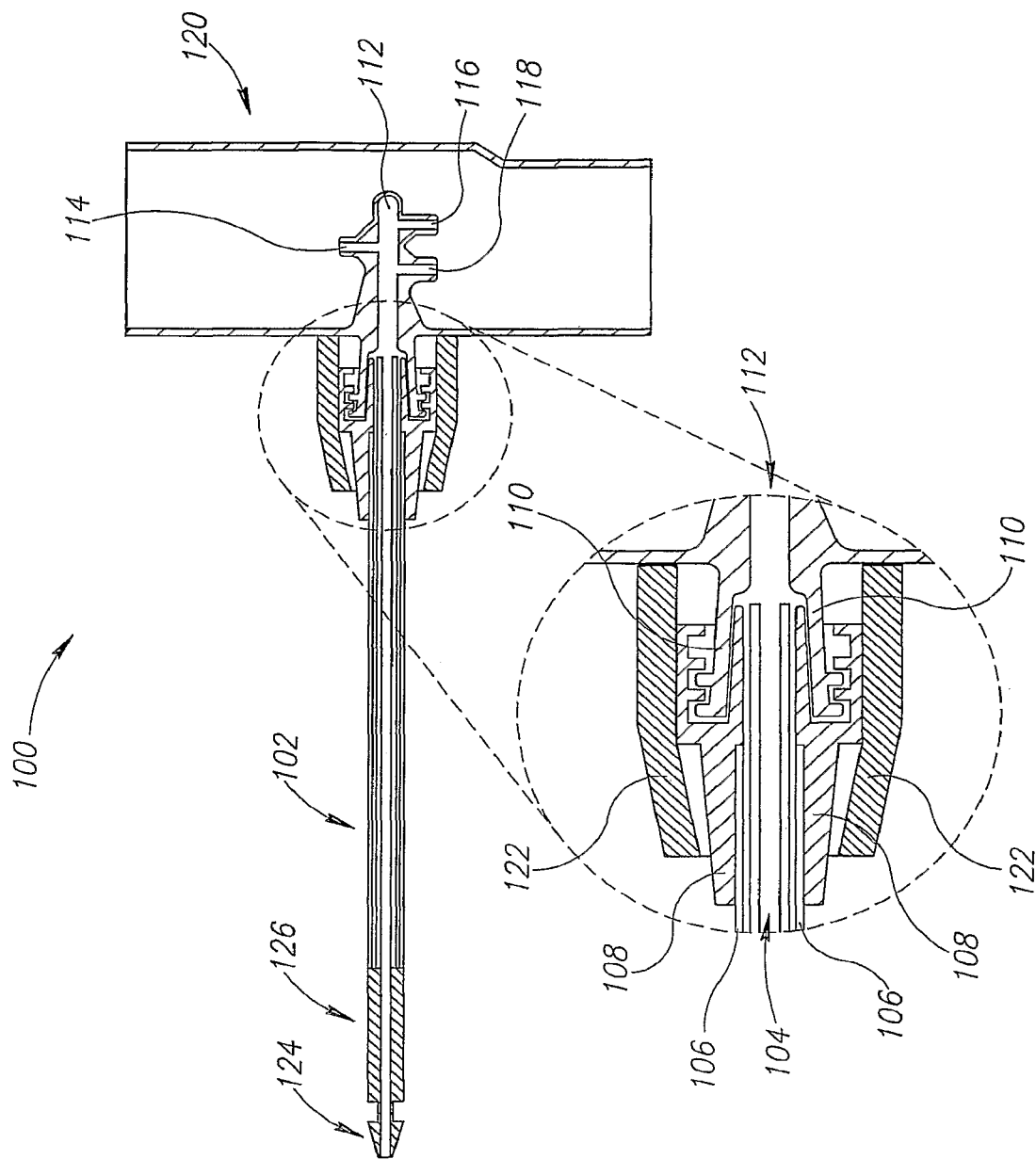
FIG. 3 shows a sectional illustration taken along section lines III-III in FIG. 2.

Reference is now made to FIG. 3, which shows a sectional illustration taken along section lines III-III in FIG. 2. The sampling system 100 includes a moisture reduction system 102, which includes a dryer tube 104 and a reinforcing element 106. The moisture reduction system 102 further includes a connector 108 that is adapted to connect the dryer tube 104 substantially adjacent to a breath sampling inlet 110. FIG. 3 particularly demonstrates an example of an essentially proximate connection between the dryer tube 104, which has a reinforcing element 106, and the airway adaptor 120 which is adapted to fit into the respiratory output device (particularly, endotracheal tube, intubation tube and the like). This essentially proximate connection is done using the connector 108, which has an inner structure that is adapted to fit the outer structure of the breath sampling inlet 110 integrally formed with the airway adaptor 120. It is noted that other appropriate connectors, inlets and/or adaptors, which may have different shapes and/or operative mechanisms, and are adapted to maintain an essentially proximate connection between a drying mechanism, such as the dryer tube 104, and a respiratory output device (such as mask, cannula, oral and/or nasal breath collectors, an endotracheal tube, intubation tube and the like) may be used. Also shown is the gripper 122, which partially covers the connector 108 and may allow grabbing the sampling system 100 without touching and possibly damaging the dryer tube 104.

Figure 4:
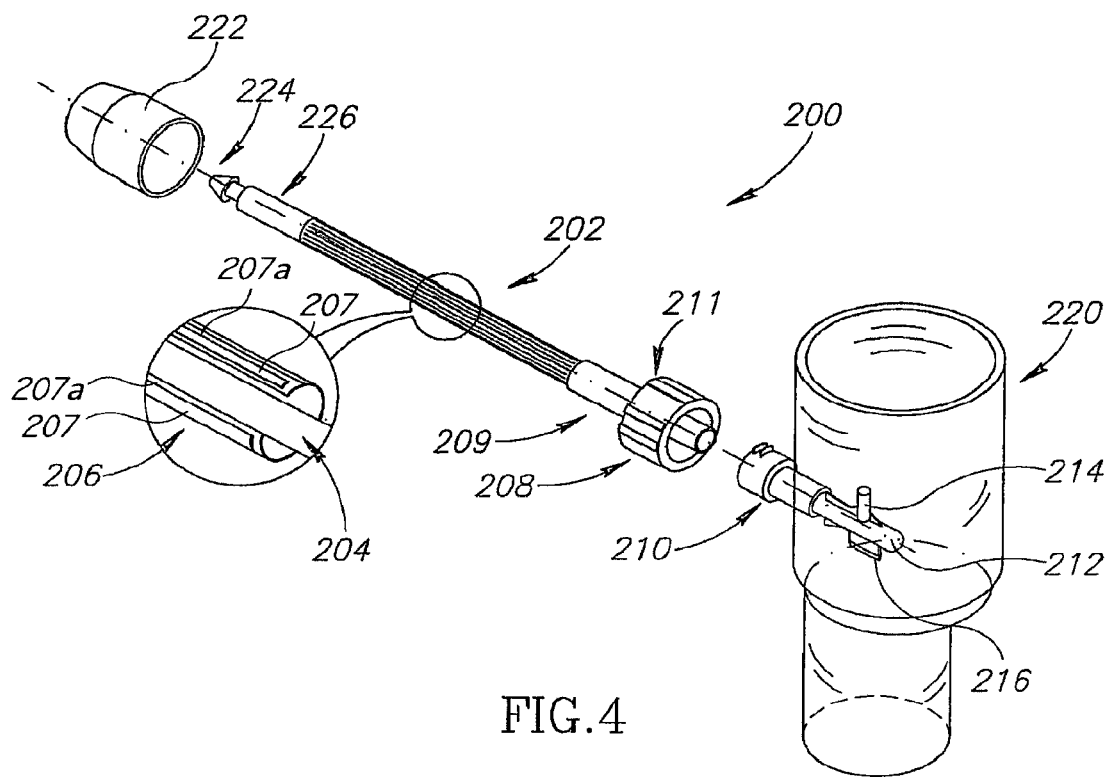
FIG. 4 schematically illustrates an exploded view of a sampling system constructed and operative in accordance with other embodiment of the present disclosure.
Figure 5:
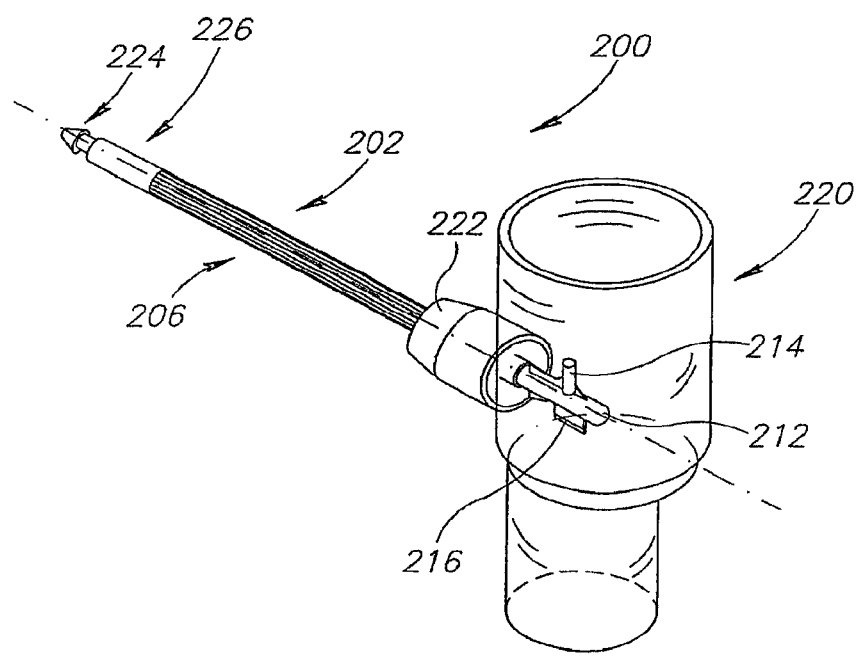
FIG. 5 schematically illustrates an assembled view of the sampling system of FIG. 4.

Reference is now made to FIG. 4, which schematically illustrates an exploded view of a sampling system constructed and operative in accordance with another embodiment of the present disclosure and to FIG. 5, which schematically illustrates an assembled view of the sampling system of FIG. 4. The sampling system 200 is adapted for sampling and analysis of exhaled breath, while reducing the exhaled breath moisture using a moisture reduction system 202 adapted to position a dryer mechanism adjacent to a connector 208 wherein the connector 208 is adapted to connect the dryer mechanism to a respiratory output device (such as a mask, cannula, oral and/or nasal breath collectors, endotracheal tube intubation tube and the like).

The sampling system 200 includes a moisture reduction system 202, which includes a dryer mechanism, particularly a dryer tube 204 and a reinforcing element 206. The dryer tube 204 is adjacent to a connector 208 that is adapted to connect the dryer tube 204 substantially adjacent to a breath sampling inlet 210. The breath sampling inlet 210 is adapted to connect between the connector 208 (which has knurls or ridges (211)) and the airway adaptor 220 which is adapted to fit into the respiratory output device (particularly, endotracheal tube, intubation tube and the like). The breath sampling inlet 210 may be integrally formed with the airway adaptor 220 (as shown) or may be attached to the airway adaptor 220. The breath sampling inlet 210 is shown (partially) within an airway adaptor 220. The breath sampling inlet 210 further includes a sampler 212 having sampling prongs 214 and 216 (shown as an open ended box, having a rectangular cross section) which are adapted to collect exhaled (and also inhaled) breath. Of course, sampler 212 may be structured differently, for example in deferent length, position within the airway adaptor 220, angle, number and position of sampling prongs and the like. The sampler 212 may include openings and/or funnel shaped collectors instead of one or more prongs and/or may include, for example one or more (for example 1, 2, 3 or more) prongs in each one of the sampling sides.

The moisture reduction system 202 further includes a gripper 222, which is adapted to (at least partially) cover the connector 208 (as shown in FIG. 5) and may allow the attendant (technician, nurse and the like) to handle the sampling system 200 without touching and possibly damaging the dryer tube 204. The moisture reduction system 202 further includes a molded-on connector 209 which may cover the end of the dryer tube 204 (adjacent to the connector 208). The molded-on connector 209 also provides a mechanical protection to the dryer tube 204 (which is often of a frail nature).

The moisture reduction system 202 further includes a molded-on connector 226 having a male adaptor 224, which is adapted to connect to the sampling tubing (not shown). The molded-on connector 226 may also cover the end of the dryer tube 204 (the opposite end from the end adjacent to the connector 208). The molded-on connector 226 also provides a mechanical protection to the dryer tube 104 (which is often of a frail nature).

It is noted that other appropriate connectors and/or adaptors, which may have different shapes and/or operative mechanisms, may be used. The sampling tubing may further include another moisture reduction system (not shown), which may be the same or different from moisture reduction system 202 and a coupler that allows the connection of the sampling system 200 to a gas analyzer such as a capnograph (not shown).

The dryer tube 204 may include any drying mechanism and/or material that is capable of reducing the moisture level in the sampling system 200 and the sampling tubes. For example, the dryer tube 204 may include Nafion® as referred to herein. In another example, the dryer tube 204 may include filters such as microporous filters or molecular sieves (material containing tiny pores of a precise and uniform size that may be used to absorb moisture). The dryer tube 204 may vary in length and/or in diameter.

The reinforcing element 206 is adapted to provide mechanical protection to the drying tube 204, for example prevent flow interruption, damaging, (partially) blocking, bending and/or collapsing of the drying tube 204. The reinforcing element 206 may cover a portion of the drying tube 204. The reinforcing element 206 may include, for example, rigid bars (207) with spaces (207*a*) therebetween (as shown in FIG. 4) or any other form of mechanical support, such as a rigid braided net (similar to that shown in FIG. 1 at 106). The connector 208 that is adapted to connect the dryer tube 204 substantially adjacent to the breath sampling inlet 210 may vary in shape and or size, for example in a way that would allow minimizing the distance between the dryer tube 104 and the breath sampling inlet 210.

The gripper 222 may also include an insulating material. The insulating material may be a thermal insulator (made for example from a foamy material) that allows maintaining relatively high temperature of the sampled breath prior to reaching the dryer tube 204. Maintaining relatively high temperature of the sampled breath will in turn reduce the condensing out of water and thus increase the efficiency of the dryer tube 204.

Figure 6:
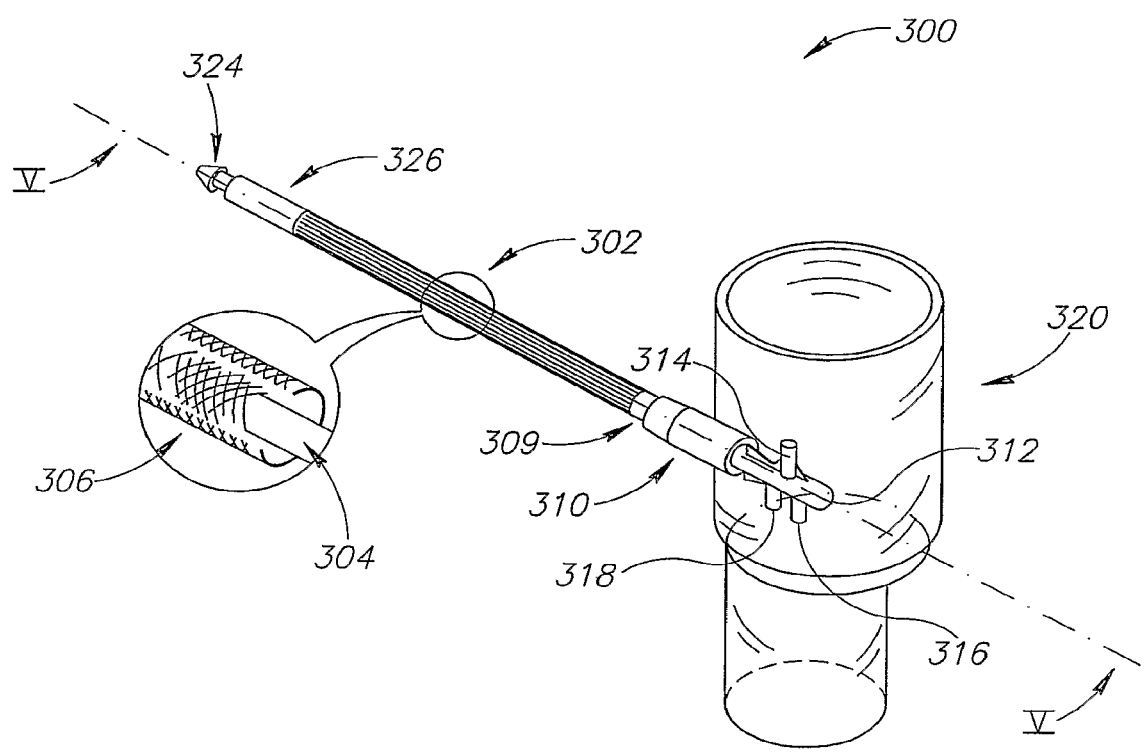
FIG. 6 schematically illustrates a sampling system constructed and operative in accordance with additional embodiments of the present disclosure.

Reference is now made to FIG. 6, which schematically illustrates a view of a sampling system constructed and operative in accordance with an additional embodiment of the present disclosure.

The sampling system 300 is adapted for sampling and analysis of exhaled breath, while reducing the exhaled breath moisture using a moisture reduction system 302 adapted to position a dryer mechanism proximate to a respiratory output device (such as a mask, cannula, oral and/or nasal breath collectors, endotracheal tube intubation tube and the like). The respiratory output device is generally located on or near the patient.

The sampling system 300 includes a moisture reduction system 302, which includes a dryer mechanism, particularly a dryer tube 304 and a reinforcing element 306.

The moisture reduction system 302 further includes a molded-on connector 309 which may cover the end of the dryer tube 304 and also provide a mechanical protection to the dryer tube 304 (which is often of a frail nature). The system 300 further includes a breath sampling inlet 310. The breath sampling inlet 310 is adapted to connect the moisture reduction system 302 (by the molded-on connector 309) substantially adjacent to the airway adaptor 320 which is adapted to fit into the respiratory output device (particularly, endotracheal tube, intubation tube and the like). FIG. 6 demonstrates a configuration in which the dryer mechanism (particularly, the moisture reduction system 302 is connected directly to the airway adaptor 320.

The breath sampling inlet 310 is integrally formed with the airway adaptor 320. The breath sampling inlet 310 may also be attached to the airway adaptor 320. The breath sampling inlet 310 is shown (partially) within an airway adaptor 320. The breath sampling inlet 310 further includes a sampler 312 having sampling prongs 314, 316 and 318 which are adapted to collect exhaled (and also inhaled) breath. Of course, sampler 312 may be structured differently, for example in deferent length, position within the airway adaptor 320, angle, number and position of sampling prongs and the like. The sampler 312 may include openings and/or funnel shaped collectors instead of one or more prongs and/or may include, for example one or more (for example 1, 2, 3 or more) prongs/openings in each one of the sampling sides.

The moisture reduction system 302 further includes a gripper (not shown), which is adapted to (at least partially) cover the breath sampling inlet 310 and may allow the attendant (technician, nurse and the like) to handle the sampling system 300 without touching and possibly damaging the dryer tube 304. The gripper may include an insulating material. The insulating material may be a thermal insulator (made for example from a foamy material) that allows maintaining relatively high temperature of the sampled breath prior to reaching the dryer tube 304.

The moisture reduction system 302 further includes a molded-on connector 326 having a male adaptor 324, which is adapted to connect to the sampling tubing (not shown). The molded-on connector 326 also provides a mechanical protection to the dryer tube 304 (which is often of a frail nature).

It is noted that other appropriate connectors and/or adaptors, which may have different shapes and/or operative mechanisms, may be used. The sampling tubing may further include another moisture reduction system (not shown), for example, a filter of molecular sieve into which certain materials are impregnated such as to form drying system which is adapted to absorb moisture and is essentially impermeable to gases. The moisture reduction system may be the same or different from moisture reduction system 102 and a coupler that allows the connection of the sampling system 100 to a gas analyzer such as a capnograph (not shown).

The dryer tube 304 may include any drying mechanism and/or material that is capable of reducing the moisture level in the sampling system 300 and the sampling tubes. For example, the dryer tube 304 may include Nafion® as referred to herein. In another example, the dryer tube 304 may include filters such as microporous filters or molecular sieves (material containing tiny pores of a precise and uniform size that may be used to absorb moisture). The dryer tube 304 may vary in length and/or in diameter.

The reinforcing element 306 is adapted to provide mechanical protection to the drying tube 304, for example prevent flow interruption, damaging, (partially) blocking, bending and/or collapsing of the drying tube 304. The reinforcing element 306 may cover a portion of the drying tube 304. The reinforcing element 306 may include, for example, a braiding net or any other form of mechanical support, such as rigid bars.

Figure 7:
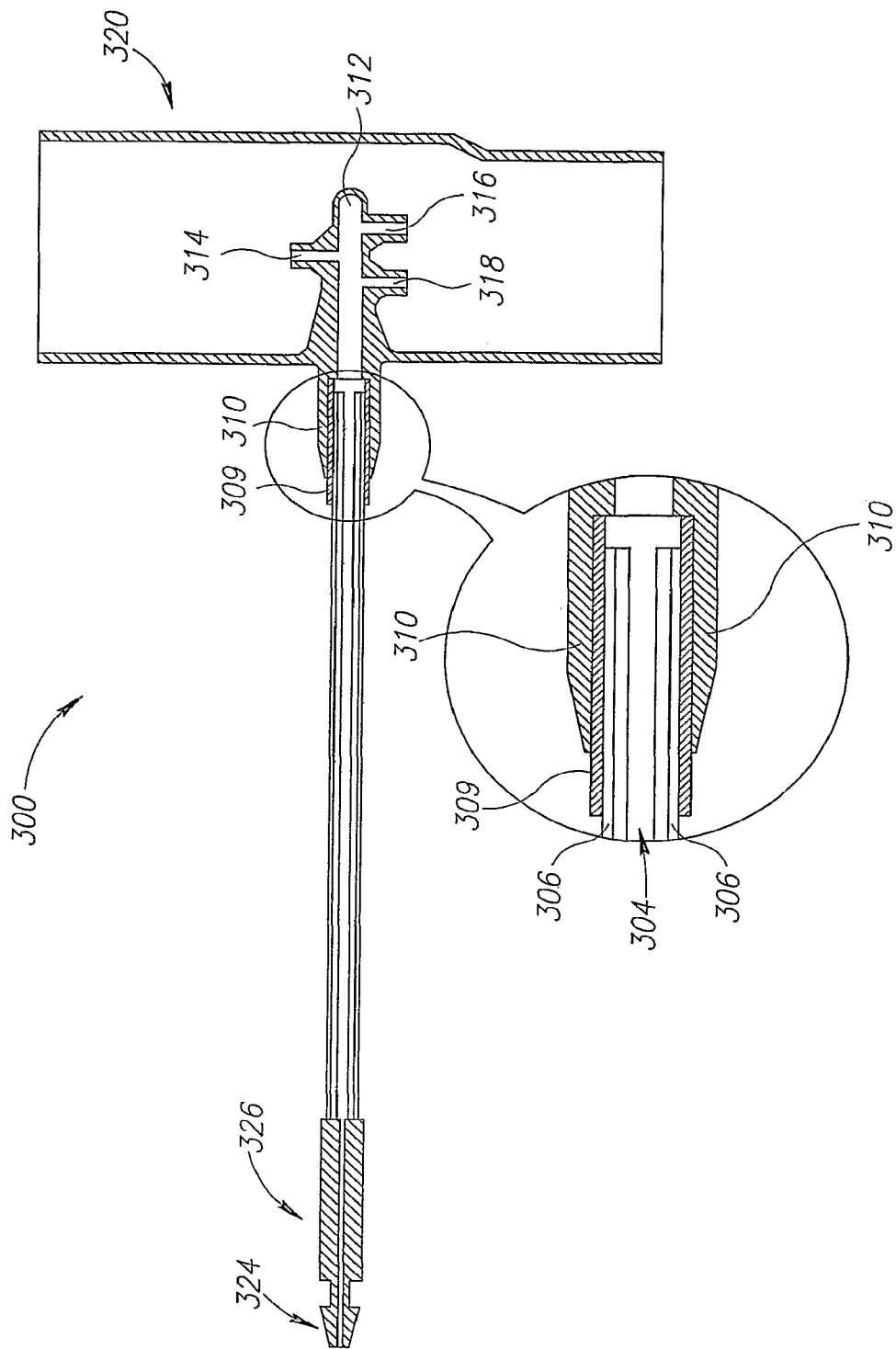
FIG. 7 shows a sectional illustration taken along section lines V-V in FIG. 4.

Reference is now made to FIG. 7, which shows a sectional illustration taken along section lines V-V in FIG. 6. The sampling system 300 includes a moisture reduction system 302, which includes a dryer tube 304 and a reinforcing element 306. The moisture reduction system 302 further includes a molded-on connector 309 which may cover the end of the dryer tube 304 and a breath sampling inlet 310. The breath sampling inlet 310 is adapted to connect the dryer tube 304 (with or without the molded-on connector 309) substantially adjacent to the airway adaptor 320 which is adapted to fit into the respiratory output device (particularly, endotracheal tube, intubation tube and the like). FIG. 3 particularly demonstrates an example of an essentially proximate connection between the dryer tube 304, which has a reinforcing element 306, and the airway adaptor 320 which is a part of the respiratory output device (particularly, endotracheal tube, intubation tube and the like). It is noted that other appropriate, inlets (which may also have the functionality of connectors) and/or adaptors, having different shapes and/or operative mechanisms, and are adapted to maintain an essentially proximate connection between a drying mechanism, such as the dryer tube 304, and a respiratory output device (such as mask, cannula, oral and/or nasal breath collectors, an endotracheal tube, intubation tube and the like) may be used.

Figure 8:
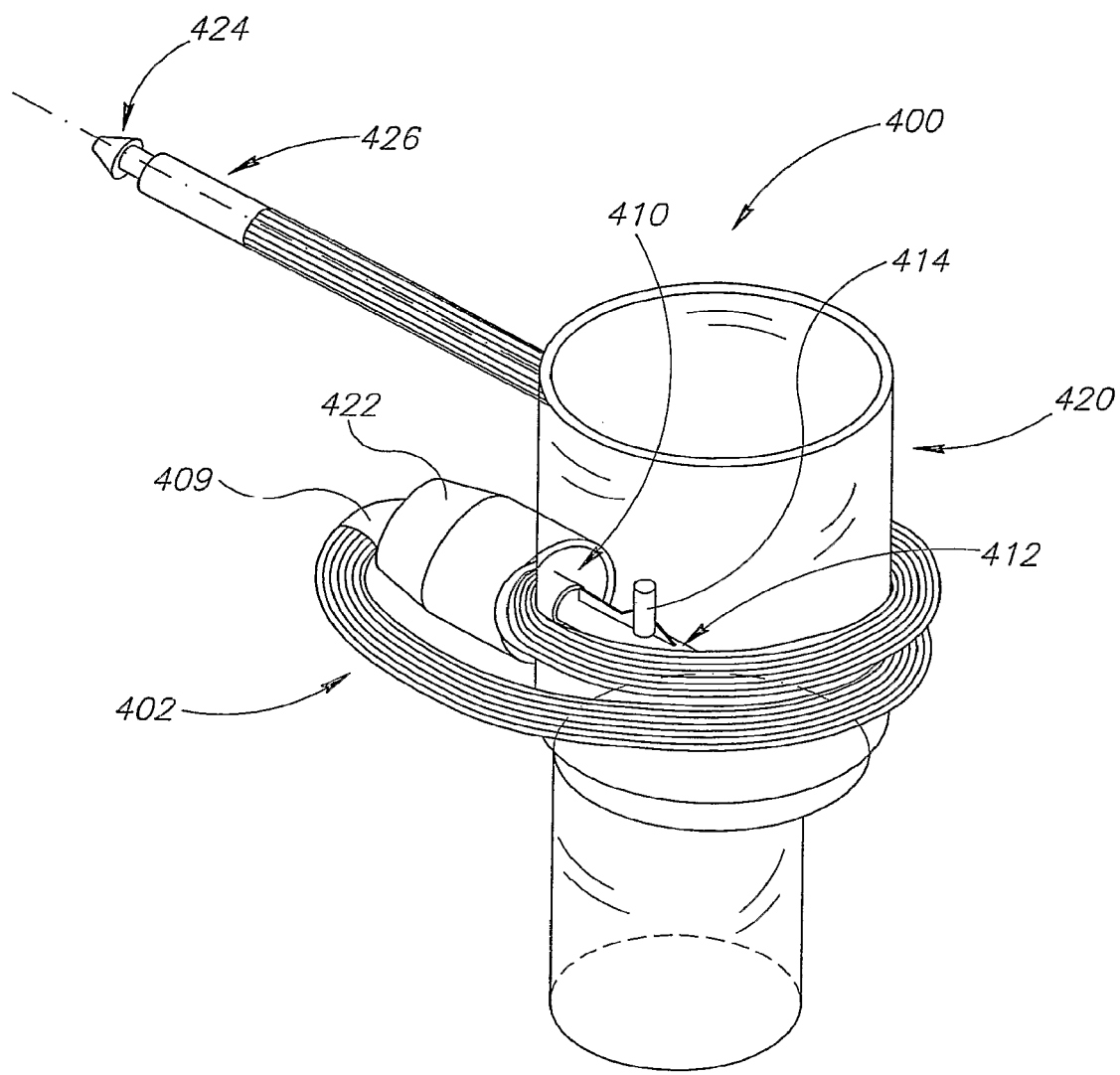
FIG. 8 shows a schematic illustration of a sampling system constructed and operative in accordance with some embodiment of the present disclosure.

Reference is now made to FIG. 8, which shows a schematic illustration of a sampling system constructed and operative in accordance with some embodiment of the present disclosure. The sampling system 400 is adapted for sampling and analysis of exhaled breath, while reducing the exhaled breath moisture using a moisture reduction system 402 (shown as a dryer tube) adapted to position a dryer mechanism proximate to a respiratory output device (such as a mask, cannula, oral and/or nasal breath collectors, endotracheal tube intubation tube and the like). The respiratory output device is generally located near the patient.

The sampling system 400 includes a moisture reduction system 402, which includes a dryer mechanism. The moisture reduction system 402 further includes a molded-on connector 409 which may cover the end of the dryer tube and also provide a mechanical protection to the dryer tube (which is often of a frail nature). The system 400 further includes a breath sampling inlet 410. The breath sampling inlet 410 is adapted to connect the moisture reduction system 402 (by the molded-on connector 409) substantially adjacent to the airway adaptor 420 which is adapted to fit into the respiratory output device (particularly, endotracheal tube, intubation tube and the like). FIG. 8 demonstrates a configuration in which the dryer mechanism (particularly, the moisture reduction system 402 is connected directly to the airway adaptor 420, similar to the moisture reduction system 302 shows in FIG. 6, however the moisture reduction system 402 is wound around the airway adaptor 420). This configuration is adapted to increase the efficiency of the dryer mechanism and reduce humidity and/or moisture in the sampled gas as by winding the moisture reduction system 402 around the airway adaptor 420, the warmed air of the patient's airway flow (from either natural breathing or artificial ventilation) heats the dryer mechanism and thus maintain a higher temperature of the humid gas.

The breath sampling inlet 410 is integrally formed with the airway adaptor 420. The breath sampling inlet 410 may also be attached to the airway adaptor 420. The breath sampling inlet 410 is shown (partially) within an airway adaptor 420. The breath sampling inlet 410 further includes a sampler 412 having sampling prong(s) 414 (only one shown, but there may be more) which is (are) adapted to collect exhaled breath. Of course, sampler 412 may be structured differently, for example in deferent length, position within the airway adaptor 420, angle, number and position of sampling prongs and the like. The sampler 412 may include openings and/or funnel shaped collectors instead of one or more prongs and/or may include, for example one or more (for example 1, 2, 3 or more) prongs/openings in each one of the sampling sides.

The moisture reduction system 402 further includes a gripper 422, which is adapted to (at least partially) cover the breath sampling inlet 410 and may allow the attendant (technician, nurse and the like) to handle the sampling system 400 without touching and possibly damaging the dryer tube. The gripper may include an insulating material. The insulating material may be a thermal insulator (made for example from a foamy material) that allows maintaining relatively high temperature of the sampled breath prior to reaching the dryer tube.

The moisture reduction system 402 further includes a molded-on connector 426 having a male adaptor 424, which is adapted to connect to the sampling tubing (not shown). The molded-on connector 426 also provides a mechanical protection to the dryer tube (which is often of a frail nature).

While certain features of the disclosure have been illustrated and described herein, many modifications, substitutions, changes, and equivalents will now occur to those skilled in the art. It is, therefore, to be understood that the appended claims are intended to cover all such modifications and changes as fall within the true spirit of the disclosure.

What is claimed is:

1. A system comprising:
  a moisture reduction system comprising a dryer tube, wherein the dryer tube comprises an inlet, an outlet, and a material extending between the inlet and the outlet and configured to absorb moisture, and wherein the material is essentially impermeable to gases;
  a respiratory device comprising an adaptor having a first central bore;
  a breath sampling inlet extending from the adaptor and configured to collect a breath sample of a patient, wherein the breath sampling inlet comprises a proximal end, a distal end, and a second central bore extending between the proximal end and the distal end;

a first connector at least partially covering an outer surface of the inlet of the dryer tube and configured to couple the dryer tube to the breath sampling inlet; and a second connector comprising a coupler configured to connect the moisture reduction system to a capnograph, and further comprising a reinforcing element disposed along at least a portion of a length of the dryer tube, wherein the dryer tube extends through the first connector and wherein the reinforcing element extends partially through the first connector.

2. The system of claim 1, wherein the breath sampling inlet is integrally formed with the adaptor.

3. The system of claim 1, wherein at least a portion of the distal end of the breath sampling inlet covers at least a portion of the first connector.

4. The system of claim 1, wherein the first connector is molded onto the inlet of the dryer tube.

5. The system of claim 1, wherein the distal end of the breath sampling inlet is tapered.

6. The system of claim 1, wherein the second central bore of the breath sampling inlet comprises a first diameter and a second diameter that is less than the first diameter such that a step is formed at a transition between the first diameter and the second diameter.

7. The system of claim 6, wherein an end of the first connector of the dryer tube abuts the step when the dryer tube is coupled to the breath sampling inlet via the first connector.

8. The system of claim 1, comprising a sampler disposed within the first central bore and forming part of the proximal end of the breath sampling inlet, wherein the sampler comprises one or more openings fluidly coupled to the second central bore and configured to collect the breath sample of the patient.

9. The system of claim 1, wherein a portion of the breath sampling inlet is within the first central bore of the adaptor.

10. The system of claim 1, wherein the dryer tube extends radially away from the adaptor.

11. The system of claim 1, wherein the dyer tube is coiled around the adaptor.

12. The system of claim 1, wherein the dryer tube material is a copolymer of tetrafluoroethylene and perfluoro-3,6-dioxa-4-methyl-7-octene sulfonic acid.

13. The system of claim 1, wherein the respiratory device comprises an endotracheal tube or an intubation tube.

14. A moisture reduction device comprising:

a dryer tube having an inlet, an outlet, and a material extending between the inlet and the outlet, wherein the material is configured to absorb moisture, and wherein the material is essentially impermeable to gases;

a first connector coupled to the inlet of the dryer tube and comprising a first end and a second end;

a second connector comprising a coupler configured to connect the moisture reduction device to a capnograph; and a breath sampling inlet extending from an adaptor of a respiratory device and configured to collect a sample breath of a patient, wherein the breath sampling inlet comprises a proximal end, a distal end, and a central bore extending between the proximal end and the distal end, and the first connector couples the dryer tube to the breath sampling inlet, further comprising a reinforcing element disposed along at least a portion of a length of the dryer tube, wherein the dryer tube extends through the first connector and wherein the reinforcing element extends partially through the first connector.

15. The moisture reduction system of claim 14, wherein the central bore comprises a first diameter and a second diameter that is smaller than the first diameter thereby forming a step at a transition between the first diameter and the second diameter, and wherein the first end of the first connector abuts the step when the dryer tube is coupled to the breath sampling inlet via the first connector.

16. A moisture reduction device comprising:

a dryer tube having an inlet, an outlet, and a material extending between the inlet and the outlet, wherein the material is configured to absorb moisture, and wherein the material is essentially impermeable to gases;

a first connector at least partially covering an outer surface of the inlet of the dryer tube;

a second connector comprising a coupler configured to connect the moisture reduction device to a capnograph; and a breath sampling inlet extending from an adaptor of a respiratory device and configured to collect a breath sample of a patient, wherein the breath sampling inlet comprises a proximal end, a distal end, and a central bore extending between the proximal end and the distal end and the first connector is configured to connect the dryer tube to the breath sampling inlet, wherein the distal end of the breath sampling inlet is tapered, further comprising a reinforcing element disposed along at least a portion of a length of the dryer tube, wherein the dryer tube extends through the first connector and wherein the reinforcing element extends partially through the first connector.

17. The moisture reduction device of claim 16, wherein the central bore comprises a first diameter and a second diameter that is smaller than the first diameter thereby forming a step at a transition between the first diameter and the second diameter, and wherein a first end of the first connector abuts the step when the dryer tube is coupled to the breath sampling inlet.

* * * * *